United States Patent [19]

Pikarski et al.

[11] Patent Number: 4,537,992
[45] Date of Patent: Aug. 27, 1985

[54] METHOD FOR REMOVAL OF NITROSOAMINE IMPURITIES FROM HERBICIDES

[75] Inventors: Michael Pikarski, Ramat-Gen; Julian Gabe, Rehovoth; Edmund Dykman, Ashdod, all of Israel

[73] Assignee: Agan Chemical Manufacturers, Ltd., Israel

[21] Appl. No.: 578,518

[22] Filed: Feb. 9, 1984

[30] Foreign Application Priority Data

Feb. 18, 1983 [IL] Israel ......................... 67948

[51] Int. Cl.$^3$ ..................... C07C 87/60; C07C 111/00
[52] U.S. Cl. ..................... 564/437; 564/441; 564/112
[58] Field of Search ............... 564/437, 441, 112, 87, 564/91; 560/21; 562/433

[56] References Cited

U.S. PATENT DOCUMENTS 4,127,610 11/1978 Eizember ........................ 564/437
4,185,035 1/1980 Eizember et al. ............... 564/437

Primary Examiner—Charles F. Warren
Assistant Examiner—Harry B. Shubin
Attorney, Agent, or Firm—Ostrolenk, Faber, Gerb & Soffen

[57] ABSTRACT

A method for removal of nitrosoamine impurities from herbicides comprising contacting a nitrosoamine containing herbicide homogeneously with 0.001% to 1.0% of a compound having the formula:

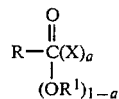

where
X equals chlorine or bromine,
$R^1$ equals lower alkyl, and
a equals zero or 1; provided that when a equals 1, then:
R equals $X_nH_{(3-n)}C(CH_2)_p$—, or

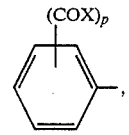

or $R^2COX$, where $R^2$ is selected from alkylene, alkenylene, alkynylene groups having 1 to 5 carbon atoms,
n equals 1 to 3, and
p equals zero, 1 or 2; and provided that when a equals zero, then:
R equals aminophenyl,
for a sufficient length of time to remove at least a substantial amount of the nitrosoamine.

12 Claims, No Drawings

METHOD FOR REMOVAL OF NITROSOAMINE IMPURITIES FROM HERBICIDES

The present invention relates to a method for removal of nitrosoamine impurities from herbicides.

BACKGROUND OF INVENTION

N-nitroso compounds, particularly alkyl nitrosoamines have been identified as carcinogens for a wide range of mamalian species. Nitrosoamines have been detected in many kinds of products such as pharmaceuticals, pesticides, cutting oils, cigarette smoke and foods like cheese, fish spices, etc.

Several classes of herbicides are known to contain small amounts of nitrosoamine impurities. Thus, for example, substituted dinitroaniline derivatives and dimethylamine salts of phenoxyalkanoic acid are major herbicides affected by this problem.

In the case of dinitroaniline derivatives, nitrosoamines are believed to be formed by the reaction of the residual nitrosating agents left over from the nitration step with the amine used in the subsequent ammination step.

For example, in the case of the typical dinitroaniline herbicide, trifluralin, the sequence of preparation is as follows:

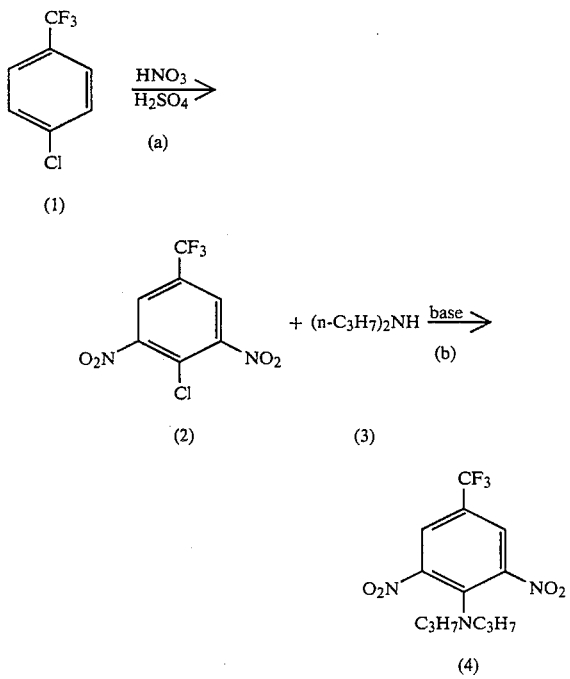

From the reaction (a), small amounts of nitrosating agents are carried along with the 4-chloro-3,5-dinitro benzotrifluoride intermediate (2) for further amination (b). These nitrosating agents, believed to be nitrogen oxides, react with the amine to form nitrosamines as in equation (c).

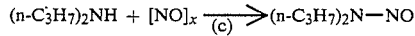

For a number of years now, pesticide manufacturers have been trying to reduce as much as possible the nitrosoamine impurities in their products. Originally, trifluralin, for example, contained from between 2 to 115 ppm nitrosoamine, but because of the carcinogenic problem, the Environmental Protection Agency (EPA) in the U.S.A. limited the allowable concentration of nitrosoamine to be 1 ppm. Most recently, this limit was reduced even further to 0.5 ppm.

This, of course, put a great burden upon dinitroaniline producers to find ways of avoiding or eliminating such trace impurities in their products.

Another problem which came to light concerning dinitroaniline herbicides such as trifluralin was that the product which immediately after manufacture complied with the EPA requirement, was found to have an increased nitrosoamine content, as much as tenfold, when stored for long periods of time such as during overseas shipping, or when formulated into agriculturally useful formulations. It is believed that prolonged storage and particularly subjecting the dinitroaniline to melting temperatures, as during the formulation process, causes formation of small amounts of nitrosamines.

The problem of complying with the EPA nitrosoamine standard has thus become twofold. First of all, to reduce the concentration to less than 0.5 ppm and secondly to prevent formation of the nitrosoamine with time or with further processing.

Basically there exist two approaches for reducing nitrosoamine content. One method is to eliminate or deactivate the nitrosating agent before it can react with any amine. This approach was taken by U.S. Pat. No. 4,120,905, which discloses the entraining of nitrosating agents from 4-chloro-3,5-dinitro benzo-trifluoride with a gas. Similarly, German Offenlegungsschrift No. 2,926,946 discloses purification of the dinitro benzene intermediate from nitrosating agents by crystallization. U.S. Pat. No. 4,331,468 teaches the prevention of nitrosoamine formation by the addition of monoalkanolamine retarding agent.

Another method for overcoming the nitrosoamine problem is to decompose the already formed nitrosoamines into harmless products. This method is applied by U.S. Pat. No. 4,127,610 by treating the dinitroaniline containing the nitrosamine impurity with bromine, chlorine or other selected brominating or chlorinating compounds. This patent, however, warns against prolonged contact between reactants which may result in further nitrosoamine formation rather than decomposition.

In a similar manner, U.S. Pat. No. 4,226,789 discloses the reduction of nitrosoamine content in dinitroanilines by heating the latter with either concentrated hydrochloric acid or HCl gas. This process does not entirely eliminate the nitrosoamine content and is prone to the generation of more nitrosoamines upon prolonged standing or heating. This process, furthermore, requires substantial quantities of HCl with comcomitant additional work up.

SUMMARY OF THE INVENTION

We have discovered that it is possible to reduce the nitrosoamine content in herbicides irreversibly, and in some instances to undetectable levels, by contacting the herbicide containing some nitrosoamine impurity homogeneously with small amounts of certain acyl halides or amino benzoate esters. The mechanism of this reaction is not quite clear but we have found that certain acyl halides and amino benzoate esters can permanently reduce the nitrosoamine content in herbicides particularly in dinitroanilines, and in many cases to levels below the 0.5 ppm range required by the EPA.

The acyl halides and amino benzoate esters useful in our invention can be represented by the formula:

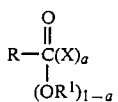

where
x equals chlorine or bromine,
$R^1$ equals lower alkyl, and
a equals zero or 1; provided that when a equals 1, then:
R equals $X_nH_{(3-n)}C(CH_2)_p$—, or

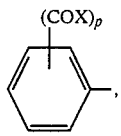

or $R^2COX$ where $R^2$ is selected from alkylene, alkenylene, alkynylene groups having 1 to 5 carbon atoms,
n equals 1 to 3, and
p equals zero, 1 or 2; and provided that when a equals zero, then,
R equals aminophenyl.

One subgroup of acyl halides to be used in this invention are the compounds having the formula:

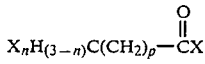

where X, n and p are as defined above.

Compounds falling in this group are chloroacetylchloride, dichloroacetyl chloride, trichloroacetyl chloride, 4-chloro-butyrchloride and the bromo analogs of all of the above compounds. Of these compounds, the dichloro- and trichloroacetylchlorides are preferred.

Another subgroup is represented by the formula:

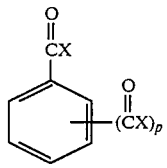

where X and p are as defined above.

Within this group can be mentioned benzoylchloride, phthaloylchloride, terephthaloylchloride, isophthaloyl chloride, trimellitic acid chloride, and the bromo analogs of these. Terephthaloyl chloride is the preferred compound because of its effectiveness, commercial availability and low vapor pressure.

Yet another subgroup which is preferred is the amino benzoate esters. Among these should be mentioned p-amino-ethyl benzoate, p-amino-methyl benzoate, p-amino-propylbenzoate, o-amino-methyl benzoate, o-amino-ethyl benzoate, o-amino-butyl benzoate, m-amino-methyl benzoate, m-amino-ethyl benzoate, m-amino-propyl benzoate, etc., the p-amino-ethyl benzoate being most preferred.

The acyl halides and amino benzoates may be added in an amount of from 0.005% to 1.0% of the dinitroaniline, preferably from 0.01% to 0.5% and most preferably from 0.05% to 0.2%. The addition is made so that the additive is homogeneously mixed with the dinitroaniline and the nitrosoamine impurity therein. This can be done by heating the mixture to a melt and thoroughly stirring. Alternatively, the dinitroaniline can be dissolved in a solvent and the additive thoroughly blended with the solution. Once the blend is homogeneous, the degradation of nitrosoamine begins. This process is of course accellerated with temperature, but this is not always necessary. Often the degradation is sufficient if the blend is kept at ambient temperature for a sufficient time. In all cases the reduction of nitrosoamines appear to be final and irreversible.

It is interesting to note, that when amino benzoates are used, the reduction or total elimination of nitrosoamines take place only if the initial concentration thereof was fairly low, in the order of about 10 ppm or less. With higher initial concentrations of nitrosoamines, for example above 30 ppm, the amino benzoates are totally ineffective in destroying nitrosoamines in dinitroaniline derivatives such as trifluralin.

It is therefore contemplated to use the amino benzoate esters in removing nitrosoamine residues which are present in concentrations of 10 ppm or less, preferably 5 ppm or less.

Nitrosoamine containing herbicides for which the process of this invention is applicable, among others, are: (the common names are in parenthesis)
5-(2-chloro-4-(trifluoromethyl)-phenoxy)-2-nitrobenzoic acid-(acifluorfen);
N-butyl-N-ethyl-2,6-dinitro-4-(trifluoromethyl)benzenamine-(benefin);
5-(2,4-dichlorophenoxy)-2-nitro-benzoic acid methyl ester-(bifenox);
4-(1,1-dimethylethyl)-N-(1-methyl-propyl)-2,6-dinitrobenzenamine-(butralin);
$N^3,N^3$-diethyl-2,4-dinitro-6-(trifluoromethyl)-1,3-benzene-diamine (dinitramine);
2,4-dinitro-6-sec-butylphenol-(dinoseb);
N-ethyl-N-(2-methyl-2-propenyl)-2,6-dinitro-4-(trifluoromethyl)-benzenamine-(ethalfluralin);
N-(2-chloroethyl)-2,6-dinitro-N-propyl-4-(trifluoromethyl)benzenamine-(fluchloralin);
4-(1-methylethyl)-2,6-dinitro-N,N-dipropylbenzenamine-(isopropalin);
4-(methylsulfonyl)-2,6-dinitro-N,N-dipropylbenzenamine-(nitralin);
2,4-dichloro-1-(4-nitrophenoxy)-benzene-(nitrofen);
4-(dipropylamino)-3,5-dinitrobenzenesulfonamide-(oxyzalin);
2-chloro-1-(3-ethoxy-4-nitrophenoxy)-4-(trifluoromethyl)benzene-(oxyfluorofen);
N-(1-ethylpropyl)-3,4-dimethyl-2,6-dinitrobenzenamine-(pendimethalin);
2,4-dinitro-$N^3,N^3$-dipropyl-6-(trifluoromethyl)-1,3-benzenediamine-(prodiamine);
N-(cyclopropylmethyl)-2,6-dinitro-N-propyl-4-(trifluoromethyl)benzenamine-(profluralin);
N-((4-dipropylamino)-3,5-dinitrophenyl)sulfonyl)-S,S-dimethylsulfilimine-(prosulfalin);
2,6-dinitro-N,N-dipropyl-4-(trifluoromethyl)benzenamine-(trifluralin).

The analysis for nitrosoamine concentration were all conducted with a thermal energy analyzer (TEA)

which has been developed for this purpose and described in J. Chromatog (1975) 351.

To determine the reduction of nitrosoamine concentration in dinitroaniline herbicides the following series of experiments were conducted. Samples of trifluralin containing a predetermined concentration of nitrosoamine were blended in the melt with a specified acyl halide or amino benzoate and kept in an oven for 16 hours at 85° C. After this time, the blend was removed from the oven and again analyzed for nitrosoamine concentration.

EXAMPLE 1

Trifluralin containing initially 56 ppm di-n-propyl nitrosoamine was treated with varying concentrations of acyl halides shown in Table 1. The nitrosoamine content subsequent to treatment is shown in the last column.

TABLE 1

| Acyl halide | Amount | Nitrosoamine (ppm) |
|---|---|---|
| benzoyl chloride | 0.1% | 6.4 |
| | 0.05% | 13.8 |
| | 0.025% | 14.4 |
| chloroacetylchloride | 0.1% | 0.1 |
| | 0.05% | 0.4 |
| | 0.025% | 2.5 |
| phthaloylchloride | 0.2% | 0.4 |
| terephthaloylchloride | 0.1% | 0.15 |
| | 0.05% | 1.2 |
| | 0.025% | 3.2 |
| adipoylchloride | 0.2% | 1.9 |

This example clearly shows the reduction of nitrosoamine content in trifluralin with the use of the compounds according to this invention. Terephthaloylchloride reduced the nitrosoamine content in trifluralin from 56 ppm to less than 0.5 ppm even when treated with as little as 0.1% terephthaloylchloride and chloroacetyl chloride achieved this at an even lower concentration, 0.05%.

EXAMPLE 2

Trifluralin containing initially 4.4 ppm di-n-propyl-nitrosoamine was treated as in example 1. The results are tabulated in Table 2.

TABLE 2

| Additive | Amount | Nitrosoamine (ppm) |
|---|---|---|
| chloroacetyl chloride | 0.1% | 0.22 |
| | 0.05% | 0.46 |
| | 0.025% | 0.66 |
| terephthaloyl chloride | 0.1% | 0.4 |
| | 0.05% | 0.7 |
| | 0.025% | 1.07 |
| p-amino-ethyl benzoate | 0.05% | 0.13 |
| | 0.025% | 0.1 |

This experiment demonstrates the advantage of the method of this invention wherein terephthaloyl chloride can reduce the nitrosoamine content from 4.4 ppm, which does not meet the EPA requirement, to less than 0.5 ppm at the concentration of only 0.05% based on trifluralin, and even at concentrations of 0.025%, chloroacetyl chloride reduces the nitrosamine content to below 1 ppm. The same holds for the aminobenzoate.

EXAMPLE 3

Trifluralin samples containing nitrosoamines at an initial concentration of 4.9 ppm were treated as in the previous examples and the results are shown in Table 3.

TABLE 3

| Additive | Amount | Nitrosoamine (ppm) |
|---|---|---|
| trichloroacetylchloride | 0.2% | 0.1 |
| 4-chlorobutyrylchloride | 0.2% | 0.2 |
| O—amino-methylbenzoate | 0.2% | 0.1 |

EXAMPLE 4

Two trifluralin samples containing 31.3 ppm and 76.7 ppm nitrosoamine respectively were treated as in the previous examples with O-amino-methyl benzoate. There was no reduction of nitrosoamine concentration even after 16 hours of heating in an oven at 85° C.

On the other hand, trifluralin containing 229 ppm nitrosoamine was treated with 0.2% benzoyl chloride for 48 hours in an oven at 85° C. The nitrosoamine content at the end of this period was 0.7 ppm.

This points out the difference between the acyl halides and amino benzoates according to this invention. Whereas the former act with a wide range of nitrosoamine concentration, the latter are effective only when the initial nitrosoamine content is relatively low.

EXAMPLE 5

Technical trifluralin having an initial nitrosoamine concentration of 3 ppm was blended with 0.2% p-amino-ethyl benzoate at 60° C. for half an hour. The product was cooled to room temperature and stored for 1 month. At the end of this period, no nitrosoamine was detectable by the thermal energy analyzer method.

EXAMPLE 6

The product of Example 5 after 1 month storage was heated for 10 hours at 85° C. Analysis via TEA for nitrosoamine at the end of this heating period showed no detectable nitrosoamine.

We claim:
1. A method for removal of nitrosoamine impurities from herbicides comprising contacting a nitrosoamine containing herbicide homogeneously with 0.001% to 1.0% of a compound having the formula:

$$R-\overset{O}{\overset{\|}{C}}(X)_a$$
$$|$$
$$(OR^1)_{1-a}$$

where
X equals chlorine or bromine,
$R^1$ equals lower alkyl, and
a equals zero or 1; provided that when a equals 1, then:
R equals $X_nH_{(3-n)}C(CH_2)_p$—, or

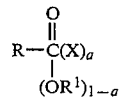

or $R^2COX$, where $R^2$ is selected from alkylene, alkenylene, alkynylene groups having 1 to 5 carbon atoms,
n equals 1 to 3, and p equals zero, 1 or 2; and provided that when a equals zero, then:

R equals aminophenyl, for a sufficient length of time to remove at least a substantial amount of the nitrosoamine.

2. A method in accordance with claim 1, wherein the herbicide is a dinitroaniline herbicide.

3. A method in accordance with claim 2, wherein the herbicide is trifluralin.

4. A method in accordance with any one of claims 1 to 3, wherein the herbicide is contacted with a compound of the formula:

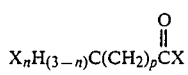

where X, n and p are as defined in claim 1.

5. A method in accordance with any one of claims 1 to 3 wherein the herbicide is contacted with a compound of the formula:

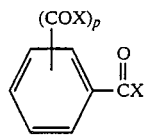

wherein X equals chlorine or bromine, and p equals zero, 1 or 2.

6. A method in accordance with any one of claims 1 to 3, wherein the herbicide is contacted with an amino-lower alkyl benzoate ester.

7. A method in accordance with claim 6 wherein the nitrosoamine impurity is less than 30 ppm.

8. A method in accordance with any one of claims 1 to 7 wherein the compound contacted with the herbicide is present in the range of 0.01 to 0.5% and preferably 0.05% to 0.2%.

9. A method in accordance with any one of claims 1 to 3 and 8 wherein the compound contacted with the herbicide is selected from, terephthalic acid, p-amino-ethyl-benzoate and 0-amino-methyl benzoate.

10. A method in accordance with any one of claims 1 to 3 and 8 wherein the compound contacted with the herbicide is selected from chloroacetylchlorides, benzoylchloride, adipoylchloride and 4-butyrylchloride.

11. A herbicide composition containing material prepared by any of the methods claimed or exemplified in the specification, and adjuvant.

12. A dinitroaniline herbicide containing less than 0.5 ppm nitrosoamine when prepared by any of the claimed methods or as described in the examples.

* * * * *